US008502016B1

(12) United States Patent
Johnston

(10) Patent No.: US 8,502,016 B1
(45) Date of Patent: Aug. 6, 2013

(54) GENOMIC ALPHA SYNUCLEIN TRANSGENIC ANIMAL

(75) Inventor: Jennifer A Johnston, Mill Valley, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 860 days.

(21) Appl. No.: 11/352,403

(22) Filed: Feb. 10, 2006

Related U.S. Application Data

(60) Provisional application No. 60/652,141, filed on Feb. 11, 2005.

(51) Int. Cl.
*G01N 33/00* (2006.01)
*A01K 67/00* (2006.01)

(52) U.S. Cl.
USPC .................................................. 800/9; 800/3

(58) Field of Classification Search
None
See application file for complete search history.

(56) References Cited

U.S. PATENT DOCUMENTS 6,504,080 B1 * 1/2003 Van Der Putten ............... 800/18

FOREIGN PATENT DOCUMENTS

| WO | WO 00/20020 A2 | 4/2000 |
| WO | WO 01/60794 A  | 8/2001 |
| WO | WO 03/015507 A1 | 2/2003 |

OTHER PUBLICATIONS

Taft et al, Trends in Genetics 22(12):649-653, 2006.*
Linder, Lab. Anim. 30(5):34-39, 2001.*
Bilbo et al, Lab. Anim. 30(1):24-29, 2001.*
Holschneider et al, Int. J. Dev. Neuroscience 18 :615-618, 2000.*
Wood. Comp. Med. 50(1): 12-15, 2000.*
Sigmund, Arterioscler. Throm. Vasc. Biol. 20:1425-1429, 2000.*
Kappel et al. Current Opinion in Biotechnology 3:558-553 1992.*
Gispert et al, Mol Cell Neurosci. 24(2):419-429, 2003.*
Scherzer et al. Hum Mol. Gen. 2003. 12(19) 2466-2475.*
Zarranz et al. Ann Neurol 2004;55:164-173.*
Chiba Falek et al. Hum Genet (2003) 113 : 426-431.*
van der Putten et al., J. Neurosci. 20:6021-6029 (2000).*
Chiba-Falek et al. , Hum. Mol. Genet. (2001) 10 (26): 3101-3109.*
Conway et al., "Acceleration of oligomerization, not fibrillization, is a shared property of both α-synuclein mutations linked to early-onset Parkinson's disease: Implications for pathogenesis and therapy," *PNAS* 97(2):571-576 (2000).
Feany et al., "A *Drosophila* model of Parkinson's disease," *Nature* 404:394-398 (2000).
Genbank Accession No. AF163864, "*Homo sapiens* SNCA isoform (SNCA) gene, complete cds, alternatively spliced," Jan. 24, 2001.
Jaenisch, "Transgenic Animals," *Science* 240:1468-1474 (1988).
Masliah et al., "Dopaminergic loss and inclusion body formation in α-synuclein mice: implications for neurodegenerative disorders," *Science* 287:1265-1269 (2000)
Touchman et al., "Human and mouse α-synuclein genes: comparative genomic sequence analysis and identification of a novel gene regulatory element," *Genomic Research* 11:78-86 (2001).
Uéda et al., "Molecular cloning of cDNA encoding an unrecognized component of amyloid in Alzheimer disease," *PNAS* 90:11282-11286 (1993).
Zarranz et al., "The new mutation, E46K, of alpha-synuclein causes Parkinson and Lewy body dementia," *Annals of Neurology* 55(2):164-173 (2004).

* cited by examiner

*Primary Examiner* — Doug Schultz
(74) *Attorney, Agent, or Firm* — Alston & Bird LLP

(57) ABSTRACT

The invention provides transgenic animals having a transgene comprising a genomic human alpha synuclein segment including six exons, five introns and at least one mutation associated with synucleinopathic disease operably linked to a human alpha synuclein promoter. The transgenic animals have characteristics of synucleinopathic disease including elevated levels of alpha synuclein in the brain, formation of intracellular deposits of alpha synuclein that have at least one, and preferably all features of Lewy bodies, formation of alpha-synuclein fragments, or phosphorylated forms of alpha synuclein, loss of neuronal cells, glial cells or oligodentricytes, impairment of motor function and/or impairment of cognitive function.

17 Claims, No Drawings

GENOMIC ALPHA SYNUCLEIN TRANSGENIC ANIMAL

CROSS-REFERENCE TO RELATED APPLICATIONS

The present application is a nonprovisional of U.S. Ser. No. 60/652,141; filed: Feb. 11, 2005, which is incorporated by reference in its entirety for all purposes.

BACKGROUND OF THE INVENTION

Alpha-synuclein brain pathology is a conspicuous feature of several neurodegenerative diseases, including Parkinson's disease (PD), dementia with Lewy bodies (DLB), diffuse Lewy body disease (DLBD), the Lewy body variant of Alzheimer's disease (LBVAD), multiple systems atrophy (MSA), and neurodegeneration with brain iron accumulation type-1 (NBIA-1). Proteinaceous insoluble inclusions in the neurons and the glia formed primarily of alpha synuclein (Lewy bodies) are common to all of these diseases.

Synucleinopathic diseases are a common cause for movement disorders and cognitive deterioration in the aging population (Galasko et al., *Clinical-neuropathological correlations in Alzheimer's disease and related dementias. Arch. Neurol.* (1994) 51:888-95). Although the incidence of these disorders continues to increase creating a serious public health problem, to date these disorders are neither curable nor preventable and understanding the causes and pathogenesis of PD is critical towards developing new treatments (Tanner et al., Epidemiology of Parkinson's disease and akinetic syndromes, *Curr. Opin. Neurol.* (2000) 13:427-30).

A number of alpha synuclein transgenic mice have been reported in which cDNA transgenes, with or without mutations associated with synucleinopathic disease, were expressed from a heterologous promoter such as PDGF or Thy-1 (see e.g., U.S. Pat. No. 6,504,080, Gispert et al., Molecular and Cellular Neuroscience 24, 419-429 (2003). A transgenic mouse having a genomic alpha synuclein construct without a mutation has been reported to lack substantial pathology (Gispert et al.). Although some of the cDNA mice show some characteristics of synucleinopathic disease, none is an entirely satisfactory model of the human condition.

SUMMARY OF THE CLAIMED INVENTION

The invention provides a transgenic nonhuman animal comprising a transgene comprising a human alpha synuclein gene comprising six exons and five introns operably linked to a human alpha synuclein promoter, the gene having at least one mutation associated with synucleinopathic disease. The alpha synuclein gene is expressed in the animal, and the animal has, or is disposed to form, intracellular deposits of human alpha synuclein. Optionally, the transgene comprises a contiguous segment of genomic DNA comprising the human alpha synuclein promoter, a transcriptional start site, the six exons and five introns and a 3' flanking sequence. Optionally, the transgenic nonhuman animal of claim 1 that is a rodent, optionally a mouse. Optionally, the transgenic nonhuman animal of claim 1 having a homozygous knocked-out endogenous alpha synuclein gene. Optionally, the transgene has a variant form of a dinucleotide repeat polymorphism located 8852 bp upstream of the transcriptional start site of the alpha synuclein gene associated with synucleinopathic disease. Optionally, the gene has a mutation associated with synucleinopathic disease in one of the six exons. Optionally, the gene has at least three mutations, and the three mutations are A30P, A53T and E46K. Optionally, the gene has a fourth mutation which is Rep1 $(TC)_{10-11}TT(TC)_{8-11}(TA)_{7-9}(CA)_{11}$. Optionally, the mutation is E46K.

In some transgenic nonhuman animals, the human alpha synuclein promoter has a mutation associated with synucleinopathic disease. Optionally, the 3' flanking sequence is at about 16.2 kb. Optionally, the transgenic nonhuman animal of claim 2, wherein the 5' flanking sequence is about 41.1 kb. Optionally, the transgenic nonhuman animal of claim 1 that has loss of neurons compared with an aged-matched nontransgenic nonhuman animal. Optionally, the transgenic nonhuman animal of claim 1, wherein the animal has motor impairment compared with an aged matched nontransgenic nonhuman animal.

The invention further provides a method of screening a compound for pharmacological activity against synucleinopathic disease. The method comprises contacting a transgenic nonhuman animal as defined in claim 1 with an agent; and determining a characteristic of synucleinopathic disease in the transgenic nonhuman animal, a change in the characteristic between the transgenic nonhuman animal and a control transgenic nonhuman animal not treated with the agent indicating the agent has pharmacological activity against synucleinopathic disease. In some methods, the characteristic is a number of alpha synuclein deposits per unit area of the brain of the animal, and a reduction in the characteristic in the contacted animal relative to the control animal indicates the compound has activity. In some methods, the characteristic is a level of alpha synuclein in the brain and a reduction in the characteristic in the contacted animal relative to the control animal indicates the compound has activity. In some methods, the characteristic is a number of neurons, glial cells or oligodentricytes, and an increase in the characteristic of the contacted animal relative to the control animal indicates the compound has the pharmacological activity. In some methods, the characteristic is a level of phosphorylated alpha-synuclein and a reduction in the level of phosphorylated alpha synuclein in the contacted animal relative to the control animal indicates the compound has the pharmacological activity. In some methods, the characteristic is a level of a proteolytic fragment of alpha synuclein and a reduction in the level of the proteolytic fragment of alpha synuclein in the contacted animal relative to the control animal indicates the compound has the pharmacological activity. In some methods, the characteristic is motor activity and an increase in the level of motor activity in the contacted animal relative to the control indicates the compound has the pharmacological activity. In some methods, the agent is administered prophylactically before the transgenic nonhuman animal has developed the deposits of alpha synuclein. In some methods, the agent is administered therapeutically after the transgenic nonhuman animal has developed the deposits of alpha synuclein.

DEFINITIONS

A Lewy body occurring in human patients has intracytoplasmic body in nerve cells formed at least in part from a water and detergent insoluble deposit of alpha synuclein characterized by staining with antibodies to alpha synuclein and often ubiquitin. The body has a spherical appearance and may also have fibrillar tangles. Fibrillar tangles may coincide with a Lewy body formed in the neurite (known as Lewy neurite). Generally, fibrillary tangles form in the axon and true spherical Lewy bodies are in the cell body. Lewy bodies are found mainly in deep layers of the neocortex and in dopaminergic neurons of the substantia nigra. Their presence in the brain disrupts the brain's normal function interrupting the action of chemical messengers including acetylcholine and dopamine.

A Lewy-like body is water/detergent-insoluble deposit of alpha synuclein found in a transgenic animal that resembles some or all of the characteristics of a Lewy body found in human patients. The preferred characteristics are a compact synuclein positive inclusion. These inclusions preferably form in an age-dependent manner. The formation of synuclein positive inclusions preferably results in observable cellular pathology, leading to loss of functionality of affected neurons. Loss of function of affected neurons can be determined through behavioral tests, neuropharmacological response evaluation and electrophysiology.

Synucleinopathic disease is characterized by degeneration of the dopaminergic system, motor alterations, cognitive impairment, and formation of Lewy bodies (LBs). (McKeith et al., *Clinical and pathological diagnosis of dementia with Lewy bodies (DLB): Report of the CDLB International Workshop, Neurology* (1996) 47:1113-24). Synucleinopathic diseases include Parkinson's disease (including idiopathic Parkinson's disease(PD)), Diffuse Lewy Body Disease (DLBD) also known as Dementia with Lewy Bodies (DLB), Combined Alzheimer's and Parkinson disease and multiple system atrophy (MSA). DLBD shares symptoms of both Alzheimer's and Parkinson's disease. DLBD differs from Parkinson's disease mainly in the location of Lewy Bodies. In DLBD Lewy Bodies form mainly in the cortex. In Parkinson's disease, they form mainly in the substantia nigra. Other Lewy Body diseases include Pure Autonomic Failure, Lewy body dysphagia, Incidental LBD, Inherited LBD (e.g., mutations of the alpha-synuclein gene, PARK3 and PARK4) and Multiple System Atrophy (e.g., Olivopontocerebellar Atrophy, Striatonigral Degeneration and Shy-Drager Syndrome).

Each nucleotide or amino acid position in a nucleic acid or protein sequence of alpha synuclein can be characterized as wildtype type or mutant. A position is characterized as wildtype if occupied by a nucleotide or amino acid most commonly occurring at that position in the human population. A mutant or variant nucleotide refers to a less frequently occurring nucleotide or amino acid in the human population. Mutant or variant nucleotides are associated with synucleinopathic disease if they occur more frequently in patients having synucleineopathic disease than in undiseased patients ($p \leq 0.05$).

The term "substantial identity" means that two amino acid sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity or higher). Preferably, residue positions which are not identical differ by conservative amino acid substitutions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra). One example of algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (NCBI) website. Typically, default program parameters can be used to perform the sequence comparison, although customized parameters can also be used. For amino acid sequences, the BLASTP program uses as defaults a word length (W) of 3, an expectation (E) of 10, and the BLOSUM62 scoring matrix (see Henikoff & Henikoff, *Proc. Natl. Acad. Sci. USA* 89, 10915 (1989)).

For purposes of classifying amino acids substitutions as conservative or non-conservative, amino acids are grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

The term "agent" is used to describe a compound that has or may have a pharmacological activity. Agents include compounds that are known drugs, compounds for which pharmacological activity has been identified but which are undergoing further therapeutic evaluation, and compounds that are members of collections and libraries that are to be screened for a pharmacological activity.

A "pharmacological" activity means that an agent exhibits an activity in a screening system that indicates that the agent is or may be useful in the prophylaxis or treatment of a disease. The screening system can be in vitro, cellular, animal or human. Agents can be described as having pharmacological activity notwithstanding that further testing may be required to establish actual prophylactic or therapeutic utility in treatment of a disease.

The term "minigene" refers to a heterologous gene construct in which one or more nonessential segments of a gene are deleted with respect to the naturally-occurring gene but at least one intronic segment is retained. Typically, deleted segments are intronic sequences of at least about 100 basepairs to several kilobases, and may span up to several tens of kilobases or more.

The term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

The terms "functional disruption" or "functionally disrupted" means that a gene locus comprises at least one mutation or structural alteration such that the functionally disrupted gene is incapable of directing the efficient expression of functional gene product. For example an endogenous alpha synuclein gene that has a neogene cassette integrated into an exon is not capable of encoding a functional protein Functional disruption can include the complete substitution of a heterologous alpha-synuclein gene locus in place of an endogenous alpha synuclein locus. An allele comprising a targeted alteration that interferes with the efficient expression of a functional gene product from the allele is referred to as "knocked out." A diploid animal can be knocked out at one or both alleles of a gene (heterozygous and homozygous knockouts).

The phrase that a molecule "specifically binds" to a target refers to a binding reaction which is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) *Antibodies, A Laboratory Manual*, Cold Spring Harbor Publications, New York, for a description of immunoassay formats and ° conditions that can be used to determine specific immunoreactivity. Specific binding between two entities means an affinity of at least $10^6$, $10^7$, $10^8$, $10^9$ M$^{-1}$, or $10^{10}$ M$^{-1}$. Affinities greater than $10^8$ M$^{-1}$ are preferred.

The term "antibody" or "immunoglobulin" is used to include intact antibodies and binding fragments thereof. Typically, fragments compete with the intact antibody from which they were derived for specific binding to an antigen fragment including separate heavy chains, light chains Fab, Fab' F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

Allelic variants of a gene are different forms of the gene naturally occurring in different individuals in the same species. Such variants occupy the same chromosomal location in different individuals. Allelic variants of a protein are different forms of a protein encoded by different allelic variants of the gene encoding the protein.

The term "about" means within the margin of error of experimental measurement. For example, a fragment of "about" 10 kb, has a fragment length of 10 kb+/−the margin of error (e.g., +/−0.1 kb) typical for by gel analysis comparing the fragment with molecular weight standards.

Compositions or methods "comprising" one or more recited elements may include other elements not specifically recited. For example, a composition that comprises alpha-SN peptide encompasses both an isolated alpha-SN peptide and alpha-SN peptide as a component of a larger polypeptide sequence.

Unless otherwise indicated any element, step, feature, or embodiment of the invention can be used in combination with any other.

DETAILED DESCRIPTION OF THE INVENTION

I. General

The invention provides transgenic nonhuman animals, particularly rodents, having a transgene comprising a genomic human alpha synuclein segment including six exons, five introns and at least one mutation associated with synucleinopathic disease operably linked to a human alpha synuclein promoter. The segment is expressed to produce human alpha synuclein. The transgenic animals have characteristics of synucleinopathic disease including elevated levels of alpha synuclein in the brain, formation of intracellular deposits of alpha synuclein that have at least one, and preferably all features of Lewy bodies, formation of alpha-synuclein fragments, or phosphorylated forms of alpha synuclein, loss of neuronal cells, glial cells or oligodentricytes, impairment of motor function and/or impairment of cognitive function.

II. Alpha Synuclein

Alpha synuclein was originally identified in human brains as the precursor protein of the non-β-amyloid component of (NAC) of AD plaques. (Ueda et al., *Proc. Natl. Acad. Sci. U.S.A.* 90 (23):11282-11286 (1993). Alpha-SN, also termed the precursor of the non-Aβ component of AD amyloid (NACP), is a peptide of 140 amino acids. Human Alpha-SN has the amino acid sequence:
MDVFMKGLSKAKEGVVAAAEKTKQGVAE-AAGKTKEGVLYVGSKTK EGVVHGVATVAEKT-KEQVTNVGGAVVTGVTAVAQKTVEGAG-SIAAATGFVKKDQ
LGKNEEGAPQEGILEDMPVDPDNEAYEMPSE EGYQDYEPEA (SEQ ID NO:1) (Uéda et al., Ibid.; GenBank accession number: P37840).

Unless otherwise indicated, reference to human alpha-synuclein protein includes the natural human amino acid sequences indicated above as well as allelic, and induced variants, thereof exhibiting at least 90% or 95% or 99% sequence identity thereto. Preferably any substitutions are conserved substitutions.

Likewise reference to the genomic DNA alpha synuclein sequence refers to the exemplary sequence of Touchman et al., Genome Research 11, 78-86 (2001) deposited under GenBank accession number AF163864 (both incorporated by reference) as well as allelic and induced variants thereof exhibiting at least 90% or 95% or 99% sequence identity thereto. Nucleotides within the coding region of genomic DNA are referred to by the codon number with respect to the above protein sequence. For example, a mutation at codon 30 in genomic DNA refers to a mutation within the three nucleotides of genomic DNA that encode amino acid 30 of the above protein. The genomic DNA sequence includes six exons and five introns. The exons are of length 161, 380, 146, 42, 143, 84 and 1107 bp and the introns of length 1270, 1052, 7372, 5773, 93050, and 2634 bp respectively in the natural human sequence of Touchman et al. The promoter occurs with a 5' flanking segment extending 10 kb from the first exon. A dinucleotide repeat polymorphism (Rep1) is located 8852 bp upstream of the transcriptional start site (i.e., within the 5 flanking region). At least five alleles are known. Longer lengths are associated with Lewy body disease.

Coding region mutations of human alpha synuclein associated with synucleinopathic disease include A30P, A53T, E46K, E83Q, A90V, and A76T. E46K (Zarranz et al., Annal. Neuol. 55, 164-173 (2004) and combinations of this mutation with others, particularly A30P and A53T are particularly preferred. The amino acid associated with synucleinopathic disease is given second. Noncoding region mutations include rs1442140 A>G, rs1372513 A>G, rs2583961 A>G, rs1372525 C>T, Rep(1), rs2583988 A>G, rs2619364 C>T, rs2619363 C>A, rs2301135 C>G, (all in the 5' flanking region), rs321647 ins G, rs10005233 A>G, rs2619372C>T, rs2583959 C>G, rs2737024C>T, IVS4 tri, rs356168A>G (all in the fourth intron) rs356200 A>G (in the 5th intron), rs356166 C>G and rs356165 C>T (in the 3' flanking region). By convention, the more frequently occurring allele is given first. RS numbers are accession numbers used for polymorphisms by the National Center for Biotechnology Information. By convention, the more frequently occurring allele is given first. Rep1 has the formula $(TC)_{10-11}TT(TC)_{8-11}(TA)_{7-9}(CA)_{10-13}$, the numerical subscript indicative of the possible number of dinucleotide repeats. Most of the variation between individuals occurs in the CA repeat. Additional mutations can be identified either by association studies demonstrating association between a mutation and familial synucleinopathic disease. Alternatively, mutations in coding regions can be identified by showing that the mutation enhances aggregation of alpha synuclein in an in vitro aggregation assay (see, e.g., Conway et al., PNAS 97 571-576 (2000)).

II. Transgenes

The gene for human alpha synuclein is contained within PAC clone 27M07 described by Touchman et al., Genome Research 11:78-86 (2001). The full genomic sequence is provided at GenBank AF163864 (incorporated by reference). The six exons encode human alpha synuclein and 5' and 3' UTRs. Transgenes preferably includes each of the full six exons and five introns. The genomic sequence encoding human alpha synuclein is operably linked to a natural alpha synuclein promoter preferably as a contiguous genomic fragment including 5' flanking sequence between the transcriptional start site and promoter region. Optionally, additional 5' flanking region 5' of the promoter is included. Additional 5' sequence can include one or more enhancer elements. Optionally, the 5' flanking sequence comprises at least 10, 20, 28.5, 41.1 or 50 kb of contiguous genomic sequence starting from the transcriptional start site. A preferred 5' flanking sequence comprises a contiguous segment of GenBank accession no. AF163864 from positions 19,040-29,776 except that nucleotide positions associated with synucleinopathic disease may be substituted as described above. Optionally, the transgene also include at least 1, 5, 10, 16.2, 20, 41.1 or 50 kb of 3' flanking sequence. 3' flanking sequence can include additional enhancer elements(s), as can introns.

The transgene preferably includes one or more mutations associated with synucleinopathic disease as described above. E46K (Zarranz et al., Annal. Neuol. 55, 164-173 (2004)0 and combinations of this mutation with others, particularly A30P and A53T are particularly preferred. The transgene also preferably includes the following Rep1 allele $(TC)_{10-11}TT(TC)_{8-11}(TA)_{7-9}(CA)_{11}$ in the 5' flanking sequence.

III. Transgenesis

Transgenic animals of the invention are preferably rodents, such as mice or rats, or insects, such as *Drosophila*. Other transgenic animals such as primates, ovines, porcines, caprines and bovines can also be used. Such transgenic animals can be produced by the same general approaches described by (Masliah et al., *Am. J. Pathol.* 148:201-10 (1996) and Feany et al., *Nature* 404:394-8 (2000)). The transgene in such animals is integrated into the genome of the animal. The transgene can be integrated in single or multiple copies. Multiple copies are generally preferred for higher expression levels. In a typical transgenic animal all germline and somatic cells include the transgene in the genome with the possible exception of a few cells that have lost the transgene as a result of spontaneous mutation or rearrangement.

For some animals, such as mice and rabbits, fertilization is performed in vivo and fertilized ova are surgically removed. In other animals, particularly bovines, it is preferable to remove ova from live or slaughterhouse animals and fertilize the ova in vitro. See DeBoer et al., WO 91/08216. Methods for culturing fertilized oocytes to the pre-implantation stage are described by Gordon et al., Methods Enzymol. 101, 414 (1984); Hogan et al., Manipulation of the Mouse Embryo: A Laboratory Manual, C.S.H.L. N.Y. (1986) (mouse embryo); Hammer et al., Nature 315, 680 (1985) (rabbit and porcine embryos); Gandolfi et al. J. Reprod. Fert. 81, 23-28 (1987); Rexroad et al., J. Anim. Sci. 66, 947-953 (1988) (ovine embryos) and Eyestone et al. J. Reprod. Fert. 85, 715-720 (1989); Camous et al., J. Reprod. Fert. 72, 779-785 (1984); and Heyman et al. Theriogenology 27, 5968 (1987) (bovine embryos) (incorporated by reference in their entirety for all purposes). Sometimes pre-implantation embryos are stored frozen for a period pending implantation. Pre-implantation embryos are transferred to the oviduct of a pseudopregnant female resulting in the birth of a transgenic or chimeric animal depending upon the stage of development when the transgene is integrated. Chimeric mammals can be bred to form true germline transgenic animals.

Alternatively, transgenes can be introduced into embryonic stem cells (ES). These cells are obtained from preimplantation embryos cultured in vitro. Bradley et al., Nature 309, 255-258 (1984) (incorporated by reference in its entirety for all purposes). Transgenes can be introduced into such cells by electroporation or microinjection. ES cells are suitable for introducing transgenes at specific chromosomal locations via homologous recombination. Transformed ES cells are combined with blastocysts from a non-human animal. The ES cells colonize the embryo and in some embryos form or contribute to the germline of the resulting chimeric animal. See Jaenisch, Science, 240, 1468-1474 (1988) (incorporated by reference in its entirety for all purposes).

Alternatively, transgenic animals can be produced by methods involving nuclear transfer. Donor nuclei are obtained from cells cultured in vitro into which a human alpha synuclein transgene is introduced using conventional methods such as Ca-phosphate transfection, microinjection or lipofection. The cells are subsequently been selected or screened for the presence of a transgene or a specific integration of a transgene (see WO 98/37183 and WO 98/39416, each incorporated by reference in their entirety for all purposes). Donor nuclei are introduced into oocytes by means of fusion, induced electrically or chemically (see any one of WO 97/07669, WO 98/30683 and WO 98/39416), or by microinjection (see WO 99/37143, incorporated by reference in its entirety for all purposes). Transplanted oocytes are subsequently cultured to develop into embryos which are subsequently implanted in the oviducts of pseudopregnant female animals, resulting in birth of transgenic offspring (see any one of WO 97/07669, WO 98/30683 and WO 98/39416).

For production of transgenic animals containing two or more transgenes, the transgenes can be introduced simultaneously using the same procedure as for a single transgene. Alternatively, the transgenes can be initially introduced into separate animals and then combined into the same genome by breeding the animals. Alternatively, a first transgenic animal is produced containing one of the transgenes. A second transgene is then introduced into fertilized ova or embryonic stem cells from that animal. Optionally, transgenes whose length would otherwise exceed about 50 kb, are constructed as overlapping fragments. Such overlapping fragments are introduced into a fertilized oocyte or embryonic stem cell simultaneously and undergo homologous recombination in vivo. See Kay et al., WO 92/03917 (incorporated by reference in its entirety for all purposes).

Optionally, endogenous nonhuman alpha synuclein alleles are functionally disrupted so that expression of endogenously encoded alpha synuclein is suppressed or eliminated, so as to not interfere or contaminate transgene-encoded human alpha synuclein.

A mouse strain having homozygously disrupted alpha synuclein alleles (B6SJL/F2 stain) is commercially available Harlan Labs Indianapolis, Ind. Commercial services for achieving knockout of any desired mouse gene by gene targeting are also available (e.g., Lexicon Genetics, or Xenogen).

Gene targeting is a method of using homologous recombination to modify a mammalian genome, can be used to introduce changes into cultured cells. By targeting a gene of interest in embryonic stem (ES) cells, these changes can be introduced into the germline of laboratory animals. The gene targeting procedure is accomplished by introducing into tissue culture cells a DNA targeting construct that has a segment that can undergo homologous combination with a target locus and which also comprises an intended sequence modification (e.g., insertion, deletion, point mutation). The treated cells are then screened for accurate targeting to identify and isolate those which have been properly targeted. A common scheme to disrupt gene function by gene targeting in ES cells is to construct a targeting construct which is designed to undergo a homologous recombination with its chromosomal counterpart in the ES cell genome. The targeting constructs are typically arranged so that they insert additional sequences, such as a positive selection marker, into coding elements of the target gene, thereby functionally disrupting it. Similar procedures can also be performed on other cell types in combination with nuclear transfer. Nuclear transfer is particularly useful for creating knockouts in species other than mice for which ES cells may not be available Polejaeva et al., Nature 407, 86-90 (2000)). Breeding of nonhuman animals which are heterozygous for a null allele may be performed to produce nonhuman animals homozygous for said null allele, so-called "knockout" animals (Donehower et al. (1992) Nature 256: 215; Science 256: 1392, incorporated herein by reference).

Optionally, transgenic animals bearing a transgene expressing alpha-synuclein can be crossed with other transgenic models of neurogenic disease, such as models of Alzheimer's disease. For example, transgenic animals bearing a transgene expressing alpha-synuclein can be crossed with transgenic animals bearing a transgene expressed APP with a FAD mutation as described by e.g., Games et al., Nature 373, 523 (1995) McConlogue et al., U.S. Pat. No. 5,612,486, Hsiao et al., Science 274, 99 (1996); Staufenbiel et al., Proc. Natl. Acad. Sci. USA 94, 13287-13292 (1997); Sturchler-Pierrat et al., Proc. Natl. Acad. Sci. USA 94, 13287-13292 (1997); Borchelt et al., Neuron 19, 939-945 (1997)). The procedure for performing such a cross is described by e.g., Masliah et al., PNAS USA 98:12245-12250 (2001), which reports a cross between transgenic mice expressing a full length alpha-synuclein with PDAPP mice as described by Games et al

IV. Characteristics of Transgenic Animals

Transgenic animals are characterized by detectable expression of human alpha synuclein in the brain. Preferably the level of human alpha synuclein expressed is at least twice the mean level of expression of endogenous alpha synuclein in aged match nontransgenic animals of the same species determined at either the mRNA or protein level. Such measurements can be made using GeneChip® or ProteinChip® arrays or the like, available from Affymetrix and Ciphergen respectively. Transgenic animals also are disposed to develop, or have, at least one characteristic of synucleinopathic disease. The transgenic animals are preferably characterized by the formation of Lewy bodies or Lewy-like bodies. The deposits preferably occur in the cytoplasm but may also be found in the nuclei, or the neurites. Preferably deposits accumulate in neurites in the olfactory bulb, the hippocampus (particularly CA3 region), the neocortex, the substantia nigra (particularly in dopaminergic neurons) and the carpus callosum. The deposits are typically spherical but can have fibrillar structures as well. Intracellular deposits can be visualized by immunohistochemistry and immunofluorescence using an antibody for human alpha synuclein, or ubiquitin (which is often attached to human alpha synuclein) or an antibody to neurofilaments (see, e.g., Conway, Biochemistry 39, 2552-2563 (2000), Masliah, Sciences 287, 1265-1269 (2000)), WO 00/20020. WO 01/60794, WO 03/015507, U.S. Pat. No. 6,504,080). Intracellular deposits can also be visualized by an electron dense appearance under immunogold electron microscopy with anti-human alpha synuclein. Aggregates of alpha synuclein can also be detected by Western blotting (Sharon et al., Neuron 37, 583-595 (2003)).

The authenticity of a Lewy-like body can be assessed by performing successive extractions in increasingly denaturing solvents. For example, brain homogenate can be extracted with Tris buffered saline (250 mM NaCl), and spun at 150, 000×g for 15 minutes. The pellet is extracted with 1% Triton-X 100 for 30 min at 4 degrees and spun as before. The resulting pellet is then extracted with 1% SDS for 30 min at 25 degrees and spun as before. Finally, the pellet is extracted with 8 M Urea/1% SDS. The profile (i.e., relative proportions) of alpha synuclein (determined by Western blotting) in the different extractions is a measure of insolubility. Preferred transgenic animals have a similar ratio of alpha synuclein in different fractions to human patients with synucleinopathic disease.

Some transgenic animals are further characterized by elevated levels of phosphorylated alpha synuclein relative to aged-matched nontransgenic controls (see PCT/US04/15836 filed May 19, 2004, incorporated by reference). Some transgenic animals are further characterized by elevated levels of C-terminal truncated fragments of alpha synuclein relative to age matched nontransgenic controls as described in application PCT/US04/15836 filed May 19, 2004. Suitable antibodies for performing immunoassays of alpha synuclein are described in copending application U.S. Ser. No. 60/518,140 filed Nov. 8, 2003 or are commercially available. Preferred transgenic animals also have reduced numbers of neuronal cells, glial cells or oligodentricytes per unit area of the brain relative to age matched control nontransgenic animals. The number of cells per unit area can be determined by immunofluorescence measurement.

Preferred animals also have impaired cognitive and motor functions relative to control age matched nontransgenic animals of the same species. Motor functions can be assessed by observation of spontaneous movement assessed by interruption of infrared beams in a contained area; reduction of vertical posture; decrease in step length determined by inking rodents feet and measuring step length over a defined length; balance, determined by time to fall from a moving rod; and weakness of distal grip strength measured using an electronic grip strength meter (see Gispert et al., Molecular and Cellular Neuroscience 24, 419-429 (2003)). Cognitive impairment can be measured using a Morris water maize test (Morris, J. Neurosci. Meth. 11:47 (1984)).

A preferred transgenic animal is normal for two to three months and then begins to exhibit changes in movement consistent with clinical symptoms of Parkinson's Disease. These changes become more severe as the animal ages. Neuropatholgical analysis preferably reveals abundant synculein positive (Lewy body-like) inclusions throughout the substantia nigra and brainstem region. In very late stage, aged animals, the Lewy inclusions preferably spread to the cortex. The discrete development of Lewy bodies in certain cell foci, and the appearance of specific clinical symptoms are advantageous for study of synucleinopathies.

V. Agents to be Screened

Agents to be screened include antibodies to alpha-synuclein, peptides of alpha-synuclein, drugs known or suspected to have activity in treating a synucleinopathic disease natural products, and combinatorial libraries. Preferred peptides of alpha-synuclein are relatively short peptides of 30, 25, 20,10 or fewer amino acid. Some peptides include amino acids 118-125 of alpha-synuclein. Some peptides include 5-20 contiguous amino acids from between positions 120 and 140 of human alpha synuclein. Optionally, an amino acid immediately on the N-terminal side of the cleavage site that generates C-terminal truncated forms of alpha-synuclein is replaced with a transition state analog amino acid that forms a nonhydrolizable bond between the two amino acids flanking the cleavage site, e.g., amino acid 119 or 122 of alpha synuclein. Examples of analogs are transition state analogs are statine, hydroxyethelene, hydroxyethelamine, AHPPA, ACHPA, and derivatives thereof. One or more amino acids of a natural alpha-synuclein sequence can also be substituted with other natural amino acids.

Natural products to be screened can also be obtained from the National Cancer Institute's Natural Product Repository, Bethesda, Md. Random libraries of peptides or other compounds can also be screened for suitability. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated herein by reference for all purposes). Peptide libraries can also be generated by phage display methods. See, e.g., Devlin, WO 91/18980. Combinatorial libraries and other compounds can initially be screened for suitability by determining their capacity to bind to alpha-synuclein, or decrease expression of human synuclein via a mechanism involving the native human synculein promoter and modifying elements 5' and 3' to the coding region of the gene.

Preferred monoclonal antibodies bind to epitopes of human alpha synuclein within residues 120-140. In some methods, multiple monoclonal antibodies having binding specificities to different epitopes are used. Such antibodies can be administered sequentially or simultaneously. Antibodies to Lewy body components other than alpha-SN can also be used. For example, antibodies can be directed to neurofilament, ubiquitin, or synphilin. Therapeutic agents also include antibodies raised against analogs of alpha-SN and fragments thereof.

VI. Assays to Measure Activity

A transgenic animal of the invention is contacted with an agent under test, and a characteristic of the transgenic animal is measured and compared with the characteristic in a contemporaneous or historical control transgenic animal. The control animal is usually an aged matched transgenic animal of the same species and same genetic lineage as the test animal. Agents are usually administered at a dosage of from 1 ng/kg to 10 mg/kg, usually from 100 µg/kg to 10 mg/kg and preferably from 500 pg/kg to 5 mg/kg.

The characteristic of the transgenic animal by which pharmacological activity of an agent is assessed can be any characteristic of the transgenic animal that is absent or present at a lesser level in an aged matched nontransgenic animal and is or resembles a characteristic of synucleinopathic disease. Suitable characteristics include the level of alpha synuclein, or fragments or phosphorylated forms thereof (protein or mRNA) in the brain or particular regions thereof as described above. A desired pharmacological activity is shown by a reduction in the level of alpha synuclein or fragments or phosphorylated animal in the test animal relative to the control. Other suitable characteristics are number of Lewy or Lewy liked bodies per unit area determined by immunofluoresence measurement. Again, a desired pharmacological activity is shown by a reduction in the number of Lewy or Lewy-like bodies in the treated transgenic animal relative to the control. Other suitable characteristics include motor or cognitive impairment. In such assays, pharmacological activity of the agent is shown by improved motor or cognitive characteristics (i.e., decrease impairment of such characteristics) relative to a comparable control transgenic animal not exposed to the agent.

Analogous strategies to those described in the screening assays can be used to determine whether existing drugs, foods, environmental toxins, and other compounds exert toxic effects via promotion of alpha-synuclein processing, phosphorylation or aggregation. Such assays are performed in the same manner as the screening assays. Toxic activity is indicated by the opposite result to pharmacological activity in the screening assays.

VII. Pharmaceutical Composition and Treatment

Patients amenable to treatment include individuals at risk of a synucleinopathic disease but not showing symptoms, as well as patients presently showing symptoms. Such diseases include Parkinson's disease (including idiopathic Parkinson's disease), DLB, DLBD, LBVAD, pure autonomic failure, Lewy body dysphagia, incidental LBD, inherited LBD (e.g., mutations of the alpha-SN gene, PARK3 and PARK4) and multiple system atrophy (e.g., olivopontocerebellar atrophy, striatonigral degeneration and Shy-Drager syndrome).

Agents having pharmacological activity are incorporated into pharmaceutical compositions including in a pharmaceutically acceptable carrier. Such pharmaceutical compositions should contain a therapeutic or prophylactic amount of at least one compound identified by the method of the present invention. The pharmaceutically acceptable carrier can be any compatible, non-toxic substance suitable to deliver the compounds to an intended host. Sterile water, alcohol, fats, waxes, and inert solids may be used as the carrier. Pharmaceutically acceptable adjuvants, buffering agents, dispersing agents, and the like may also be incorporated into the pharmaceutical compositions. Preparation of pharmaceutical conditions incorporating active agents is well described in the medical and scientific literature. See, for example, Remington's Pharmaceutical Sciences, Mack Publishing Company, Easton, Pa., 16th Ed., 1982, the disclosure of which is incorporated herein by reference.

The pharmaceutical compositions just described are suitable for systemic administration to the host, including parenteral, topical, and oral administration. The pharmaceutical compositions may be administered parenterally, i.e. subcutaneously, intramuscularly, or intravenously. Thus, the present invention provides compositions for administration to a host, where the compositions comprise a pharmaceutically acceptable solution of the identified compound in an acceptable carrier, as described above.

EXAMPLES

1. Production of α-Synuclein (SNCA) Genomic mouse

This example describes the formation of founder lines of α-synuclein (SNCA) over-expressing mice using bacterial or P1-derived artificial chromosome (BAC and PAC) clones containing either the human (AF163864, RPCI-1 library PAC 27M07, RZDP, 145606 bp) or mouse loci (AF163865, strain 129/SvJ BAC 155120, RW4 cell lines; Genome Systems, 118777 bp). The former are bred onto homozygous knockout mice (C57BL/6JolaHsd, a population of the inbred strain C57BL/6J) to create a humanized SNCA over-expressing mouse model.

Experimental Overview

DNA Constructs and DNA Manipulation.

BAC and PAC clones are isolated from public and commercial libraries (Genome Systems, St Louis, Mo. and RZPD, the resource Center of the German Genome Project. Specifically, BAC RP11-458H10 was obtained from Invitrogen. They are maxi-prepped for DNA and tested for SNCA content by PCR, including primers specific for SNCA exons 1 and 6, >10 kb of endogenous promoter and 3' UTR. Additional restriction digestion and Southern blot analysis/hybridization will be used to check clone integrity (and prior injection), as routine manipulation of large DNA fragment can cause random fragmentation.

Genomic Insert Isolation

BAC and PAC inserts are isolated from vector by digestion of 25 μg is of each plasmid with rare cutter restriction endonucleases, e.g. digestion performed with Not I at 37° C. for 2 hours (whenever possible, large-bore pipette tips were used to help minimize shearing). Inserts are purified by pulse-field gel electrophoresis (PFGE), the digestion products loaded into the preparative well of a 1% low-melt agarose contour-clamped homogeneous electric field (CHEF) gel (in 0.5×Tris Borate-EDTA). A 10-1 μL quantity of the digestion product is run in lanes on either side of the preparative well to permit isolation of the insert without having to expose DNA to ethidium bromide. PFGE is performed for ~16 hours at 4° C., using a field strength of 5 V/cm and switch time ramping from 5 to 15 seconds (Bio-Rad CHEF DR II apparatus). Following PFGE, the ~418 and ~145 kb inserts are identified by cutting each gel into thirds, removing the middle third containing the insert, and staining only the 2 flanking portions of the gel with ethidium bromide. Notches are cut in the flanking gel sections to indicate where the insert has run, the gel reassembled, and an unstained gel slice containing the insert excised and stored at 4° C. in 50 mmol/L EDTA.

Transgenic Mice

In preparation for microinjection, a 4-mm piece of gel containing the BAC or PAC insert is equilibrated with high-salt injection buffer (100 mmol/L NaCl, 10 mmol/L Tris pH 8.0, 250 μmol/L EDTA) for 2 hours at 4° C. The gel slice is removed from buffer, transferred to a microfuge tube, and melted at 65° C. for 10 minutes. The sample is then to be equilibrated at 45° C. for 5 minutes, and digested with 2 U of gelase (Epicentre) at 45° C. for 1 hour. Undigested agarose is removed by centrifuging the sample at 2,000 rpm at room temperature for 5 minutes and transferring the top 90% to a new microfuge tube. DNA quality and quantity is estimated by spectrophotometry at 260/280 nm, and by running a small amount of the restriction digested, purified insert on an agarose gel. The final concentration is adjusted to 1 ng/μL using high-salt injection buffer. Samples can be stored at 4° C. although DNA prepared 'fresh' is optimum.

Two methods can be employed to create transgenic mice: 1) Microinjection of fertilized mouse eggs (FVB) can be performed and ~10 independent founder lines identified by Taqman/ABI700 quantitative PCR and by Southern analysis of EcoRI-digested tail DNA using probes specific for SNCA. Alternatively, 2) 250 ng of the BAC or PAC insert is co-electroporated into RW4 ES cells (strain 129/SvJ) along with 20 μg of a linearized PGK-Neo plasmid. Selection with 300 μg/mL G418 performed for 6 days, and G418-resistant ES clones obtained. Again, PCR and Southern analysis are performed to identify ES clones carrying a stably integrated transgene. One or more of these clones (high and low SNCA expressors) are then injected into e2.5 C57B1/6J blastocysts. We will generate ~10 chimeras of ~70% chimerism or better (based on coat color).

Expression Analyses

Copy number, transgene integration site and expression are checked using a number of approaches. First, copy number of SNCA genomic DNA and α-synuclein mRNA are assessed using human or mouse specific Taqman probes on an ABI 7900 (Applied Biosystems). Restriction digestion of genomic DNA and Southern blotting/hybridization are employed to ensure only one site of transgene incorporation, verified using duel-color fluorescent in-situ hybridization (FISH) of metaphase spreads, with a mouse chromosome 6 probe (endogenous mouse SNCA is on chromosome 6, and is an important consideration in the creation of a humanized mouse on C57BL/6JolaHsd). Northern analysis using radioactive SNCA probe is used to check expression levels and integrity of the transgenic RNA message versus the endogenous SNCA gene. Western blotting from brain tissue using human-specific and mouse α-synuclein antibody (LB509) confirms over-expression of the transgene protein.

It will be apparent to one of ordinary skill in the art that many changes and modifications can be made thereto without departing from the spirit or scope of the appended claims. Unless otherwise apparent from the context, any step, feature, embodiment, or aspect can be used in combination with any other. All publications (including patents and citations to GenBank and the like) and patent applications mentioned in this specification are herein incorporated by reference to the same extent as if each individual publication or patent application was specifically and individually indicated to be incorporated by reference.

SEQUENCE LISTING

```
<160> NUMBER OF SEQ ID NOS: 1

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140
```

5. The transgenic mouse of claim 2, wherein the 3' flanking sequence is at about 16.2 kb.

6. The transgenic mouse of claim 2, wherein the 5' flanking sequence is about 41.1 kb.

7. The transgenic mouse of claim 1 that has loss of neurons compared with an aged-matched nontransgenic rodent.

8. The transgenic mouse of claim 1, wherein the mouse has motor impairment compared with an aged matched nontransgenic mouse.

9. A method of screening a compound for pharmacological activity against synucleinopathic disease, comprising:
   contacting a transgenic rodent as defined in claim 1 with an agent; and
   determining a characteristic of synucleinopathic disease in the transgenic mouse, a change in the characteristic between the transgenic mouse and a control transgenic mouse not treated with the agent indicating the agent has pharmacological activity against synucleinopathic disease.

10. The method of claim 9, wherein the characteristic is a number of alpha synuclein deposits per unit area of the brain of the mouse, and a reduction in the characteristic in the contacted mouse relative to the control mouse indicates the compound has activity.

11. The method of claim 9, wherein the characteristic is a level of alpha synuclein in the brain and a reduction in the characteristic in the contacted mouse relative to the control mouse indicates the compound has activity.

12. The method of claim 9, wherein the characteristic is a number of neurons, glial cells or oligodentricytes, and an

What is claimed is:

1. A transgenic mouse comprising a transgene comprising a human alpha synuclein gene comprising six exons and five introns operably linked to a human alpha synuclein promoter, the transgene having E46K and Rep1 mutations, whereby the alpha synuclein gene is expressed in therodent, and the mouse has, or is disposed to form, intracellular deposits of human alpha synuclein.

2. The transgenic mouse of claim 1 wherein the transgene comprises a contiguous segment of genomic DNA comprising the human alpha synuclein promoter, a transcriptional start site, the six exons and five introns and a 3' flanking sequence.

3. The transgenic mouse of claim 1 having a homozygous knocked-out endogenous alpha synuclein gene.

4. The transgenic mouse of claim 1, wherein the transgene also includes A30P, and A53T mutations.

increase in the characteristic of the contacted mouse relative to the control mouse indicates the compound has the pharmacological activity.

13. The method of claim 9, wherein the characteristic is a level of phosphorylated alpha-synuclein and a reduction in the level of phosphorylated alpha synuclein in the contacted mouse relative to the control mouse indicates the compound has the pharmacological activity.

14. The method of claim 9, wherein the characteristic is a level of a proteolytic fragment of alpha synuclein and a reduction in the level of the proteolytic fragment of alpha synuclein in the contacted mouse relative to the control mouse indicates the compound has the pharmacological activity.

15. The method of claim 9, wherein the characteristic is motor activity and an increase in the level of motor activity in the contacted mouse relative to the control indicates the compound has the pharmacological activity.

16. The method of claim 9, wherein the agent is administered prophylactically before the transgenic mouse has developed the deposits of alpha synuclein.

17. The method of claim 9, wherein the agent is administered therapeutically after the transgenic mouse has developed the deposits of alpha synuclein.

* * * * *